United States Patent
Kim et al.

(10) Patent No.: US 12,311,202 B2
(45) Date of Patent: May 27, 2025

(54) ULTRASONIC POWERED NEURAL STIMULATING DEVICE WITHOUT POWER SOURCES AND LEAD WIRES

(71) Applicant: RESEARCH & BUSINESS FOUNDATION SUNGKYUNKWAN UNIVERSITY, Suwon-si (KR)

(72) Inventors: Sang Woo Kim, Yongin-si (KR); Young Jun Kim, Daejeon (KR); Woo Seok Kang, Suwon-si (KR); So Hee Kim, Hwaseong-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 234 days.

(21) Appl. No.: 17/888,872

(22) Filed: Aug. 16, 2022

(65) Prior Publication Data

US 2023/0059692 A1 Feb. 23, 2023

(30) Foreign Application Priority Data

Aug. 19, 2021 (KR) .................. 10-2021-0109224

(51) Int. Cl.
*A61N 7/00* (2006.01)

(52) U.S. Cl.
CPC ........ *A61N 7/00* (2013.01); *A61N 2007/0026* (2013.01)

(58) Field of Classification Search
CPC .......................... A61N 7/00; A61N 2007/0026
See application file for complete search history.

(56) References Cited

U.S. PATENT DOCUMENTS

| 2007/0293908 | A1* | 12/2007 | Cowan | A61N 1/0534 607/45 |
| 2018/0028841 | A1* | 2/2018 | Konofagou | A61B 8/085 |
| 2020/0229862 | A1* | 7/2020 | Ollerenshaw | A61K 31/00 |

* cited by examiner

*Primary Examiner* — Amal Aly Farag
(74) *Attorney, Agent, or Firm* — NSIP Law

(57) ABSTRACT

The present disclosure relates to an ultrasonic powered neural stimulating device without power sources and lead wires, and specifically, to a porous polymer stimulating portion-based ultrasonic powered neural stimulation and regeneration technology without the power sources and the lead wires. According to the present disclosure, a technology that may overcome limitations of a human implantable neural stimulating device is able to be secured, and it is expected that a new method for neural stimulation is presented.

4 Claims, 3 Drawing Sheets

ULTRASONIC POWERED NEURAL STIMULATING DEVICE WITHOUT POWER SOURCES AND LEAD WIRES

CROSS-REFERENCE TO RELATED APPLICATIONS

This application claims the benefit under 35 USC 119(a) of Korean Patent Application No. 10-2021-0109224 filed on Aug. 19, 2021, in the Korean Intellectual Property Office, the entire disclosure of which is incorporated herein by reference for all purposes.

BACKGROUND

Field

The present disclosure relates to an ultrasonic powered neural stimulating device without power sources and lead wires, and specifically, to a porous polymer stimulating portion-based ultrasonic powered neural stimulation and regeneration technology without power sources and lead wires.

Description of Related Art

Recently, geriatric diseases caused by aging have become a problem, and a human implantable medical device technology for a continuous treatment of such diseases is in the spotlight. Such an implantable medical device is largely composed of a power source, a lead wire, and a stimulating portion. The power source composed of a battery and a circuit generates an electrical signal, delivers energy to an area to be stimulated via the lead wire, and delivers the electrical signal directly via the stimulating portion. However, the power source has disadvantages in that it is difficult to miniaturize the same due to a volume occupied by the battery and an area in which the power source is inserted is limited. In addition, in a case of the lead wire, inflammation of surrounding tissues is caused and there is a risk of disconnection. Further, because the stimulating portion uses metal and a silicon material, side effects due to differences in mechanical properties with the tissues are caused.

The above limitations are particularly problematic for a neural stimulating device, which is a type of human implantable medical device. In a case of widely known a spinal cord stimulator or a pacemaker, an insertion position is secured, thereby minimizing side effects. However, in a case of the neural stimulating device, an insertion space is insufficient and the neural stimulating device is inserted in an area with a lot of movement, so that the side effects of the lead wire are noticeable. In addition, a cuff electrode, which is the stimulating portion utilized in the neural stimulating device, is a medical device in a form of a cylinder that surrounds a nerve. An operation to stably connect the cuff electrode to the thin nerve is very complicated, and surgery to remove the cuff electrode is necessary after a treatment is finished.

Because of the problems of the prior art described above, there is a need for a new electrical stimulation method, which is able to be applied anywhere in a body and does not burden a patient, with a small volume occupied by the power source, without the lead wire, and the limitations of the cuff electrode resolved.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to overcome the limitations of the prior art and furthermore propose a new scheme by proposing a porous polymer stimulating portion-based ultrasonic powered neural stimulation and regeneration technology without power sources and lead wires.

Purposes in accordance with the present disclosure are not limited to the above-mentioned purpose. Other purposes and advantages in accordance with the present disclosure as not mentioned above may be understood from following descriptions and more clearly understood from embodiments in accordance with the present disclosure. Further, it will be readily appreciated that the purposes and advantages in accordance with the present disclosure may be realized by features and combinations thereof as disclosed in the claims.

A first aspect of the present disclosure provides an ultrasonic powered neural stimulating device without power sources and lead wires including: a time-limited polymer film of a porous structure inserted into a body and wound around a nerve; and an ultrasound generator for generating an ultrasound outside the body and applying the ultrasound to the nerve.

In one implementation of the first aspect, the time-limited polymer film of the porous structure includes at least one of polylactic acid (PLA), polycaprolactone (PCL), poly(vinyl alcohol) (PVA), polylactide-co-glycolide (PLGA), or poly(3-hydroxybutyrate-co-3-hydroxyvalerate) (PHBV).

In one implementation of the first aspect, a wavelength of the ultrasound is equal to or greater than a thickness of the time-limited polymer film of the porous structure. When the wavelength of the ultrasound is equal to or greater than the thickness of the time-limited polymer film of the porous structure, a change in the thickness occurs while the ultrasound passes through the polymer film, and a change in a dielectric constant occurs based on the change in the thickness, and an electric field is generated by the change in the dielectric constant so as to stimulate the nerve.

In one implementation of the first aspect, the ultrasound generator generates an ultrasound having a frequency in a range from 20 to 50 kHz so as to perform a neural stimulation treatment.

In one implementation of the first aspect, the ultrasound generator decomposes the time-limited polymer of the porous structure by applying high intensity focused ultrasound (HIFU) having a frequency equal to or higher than 4 MHz to the polymer.

A second aspect of the present disclosure provides an ultrasonic powered neural stimulating device without power sources and lead wires including: a time-limited polymer film of a porous structure inserted into a body and wound around a nerve; a high-k material embedded in the time-limited polymer film of the porous structure; and an ultrasound generator for generating an ultrasound outside the body and applying the ultrasound to the nerve.

In one implementation of the second aspect, the time-limited polymer film of the porous structure includes at least one of polylactic acid (PLA), polycaprolactone (PCL), poly(vinyl alcohol) (PVA), polylactide-co-glycolide (PLGA), or poly(3-hydroxybutyrate-co-3-hydroxyvalerate) (PHBV).

In one implementation of the second aspect, the high-k material includes at least one of barium titanate (BTO) or calcium copper titanate (CCTO).

In one implementation of the second aspect, a wavelength of the ultrasound is equal to or greater than a thickness of the time-limited polymer film of the porous structure. When the wavelength of the ultrasound is equal to or greater than the thickness of the time-limited polymer film of the porous structure, a change in the thickness occurs while the ultrasound passes through the polymer film, and a change in a dielectric constant occurs based on the change in the thickness, and an electric field is generated by the change in the dielectric constant so as to stimulate the nerve.

In one implementation of the second aspect, the ultrasound generator generates an ultrasound having a frequency in a range from 20 to 50 kHz so as to perform a neural stimulation treatment.

In one implementation of the second aspect, the ultrasound generator decomposes the time-limited polymer of the porous structure by applying high intensity focused ultrasound (HIFU) having a frequency equal to or higher than 4 MHz to the polymer.

A third aspect of the present disclosure provides an ultrasonic powered neural stimulating device without power sources and lead wires including: a time-limited polymer film of a porous structure inserted into a body and wound around a nerve; a high-k material embedded in the time-limited polymer film of the porous structure; and an ultrasound generator for generating an ultrasound outside the body and applying the ultrasound to the nerve, wherein the time-limited polymer film of the porous structure is polylactic acid (PLA), wherein the high-k material is barium titanate (BTO), wherein an ultrasound having a frequency in a range from 20 to 50 kHz is able to be generated to perform a neural stimulation treatment, wherein the time-limited polymer of the porous structure is able to be decomposed by being applied with high intensity focused ultrasound (HIFU) having a frequency equal to or higher than 4 MHz.

According to the present disclosure, it is expected that a technology that may overcome the limitations of the human implantable neural stimulating device may be secured and a new method for neural stimulation may be proposed.

In addition to the effects as described above, specific effects in accordance with the present disclosure will be described together with following detailed descriptions for carrying out the disclosure.

Figure 1:
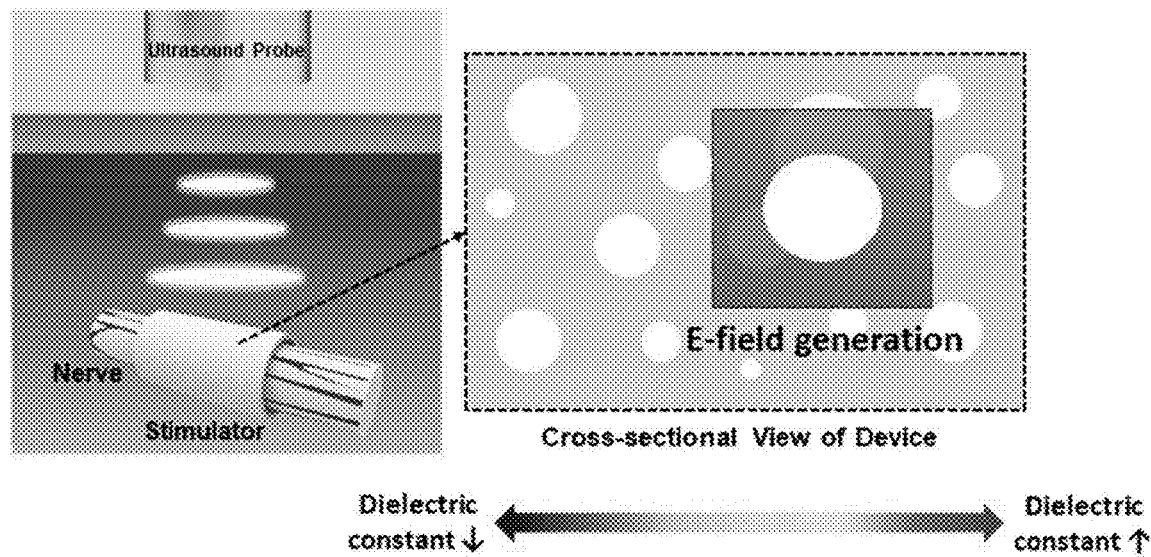
FIG. 1 shows a configuration and an operation principle of a porous time-limited polymer-based ultrasonic powered neural stimulating device according to an embodiment of the present disclosure.

Various embodiments will now be described with reference to the drawings. Like reference numerals are used throughout the drawings to refer to like elements. Herein, for purposes of illustration, various descriptions are presented to provide an understanding of the present disclosure. However, it is evident that such embodiments may be practiced without such specific descriptions. In other examples, well-known structures and devices are presented in a block diagram form in order to facilitate the description of the embodiments.

DETAILED DESCRIPTIONS

For simplicity and clarity of illustration, elements in the figures are not necessarily drawn to scale. The same reference numbers in different figures represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entirety of list of elements and may not modify the individual elements of the list. When referring to "C to D", this means C inclusive to D inclusive unless otherwise specified.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

An ultrasonic powered neural stimulating device without power sources and lead wires according to the present disclosure has no restrictions on a position to be inserted in a body, so that the device may be used for a treatment of various neuropathy and a nerve regeneration. It is to provide a new type of neural stimulating technology that does not burden a patient as such device is able to be miniaturized because a separate power source such as a battery is not required because of a simple surgical procedure and an ultrasonic power, and does not require a reoperation because the device disappears naturally using a time-limited material without a need to remove the device from the body after the treatment is finished.

FIG. 1 shows a configuration and an operation principle of a porous time-limited polymer-based ultrasonic powered neural stimulating device according to an embodiment of the present disclosure.

The ultrasonic powered neural stimulating device without the power sources and the lead wires according to an embodiment of the present disclosure includes: a time-limited polymer film of a porous structure that is inserted into a body and wound around a nerve; and an ultrasound generator that generates an ultrasound and applies the ultrasound to the polymer film from the outside of the body.

The time-limited polymer film of the porous structure includes at least one of polylactic acid (PLA), polycaprolactone (PCL), poly(vinyl alcohol) (PVA), polylactide-co-glycolide (PLGA), or poly(3-hydroxybutyrate-co-3-hydroxyvalerate) (PHBV).

In a case of a porous material, a volume fraction of each of internal air and the material affects a dielectric constant. When a mechanical force is applied to the porous material from the outside, the volume fraction of the internal air decreases and the volume fraction of the material increases, and as a result, the dielectric constant of an entirety of the material increases.

When a wavelength of the ultrasound is greater than a thickness of a medium, the ultrasound causes a change in thickness while passing through the medium. The ultrasound generates mechanical vibration while passing through the porous material, and the dielectric constant increases or decreases based on the change in the thickness. It is a feature of the present disclosure to wind the time-limited polymer film of the porous structure around the nerve and try to stimulate the nerve using an electric field generated when the ultrasound is applied to the nerve from the outside using the above fact. Because the nerve has conductivity, electric charges are induced based on the external electric field. When a value of the electric charge induction exceeds a threshold, neural stimulation is able to be achieved.

In summary, in a case of the present disclosure, an ultrasound having a wavelength equal to or greater than the thickness of the time-limited polymer film of the porous structure is used as the ultrasound. When the wavelength of the ultrasound is equal to or greater than the thickness of the time-limited polymer film of the porous structure, the ultrasound causes the change in the thickness while passing through the polymer film, and the change in the dielectric constant occurs based on the change in the thickness, so that the electric field may be generated and the neural stimulation may be achieved.

The ultrasound generator generates an ultrasound having a frequency in a range from 20 to 50 kHz to perform a neural stimulation treatment. In this case, energy of the ultrasound is about 1 W/cm$^2$.

The ultrasound generator may decompose the time-limited polymer of the porous structure by applying high intensity focused ultrasound (HIFU) having a frequency equal to or higher than 4 MHz to the polymer. In this case, the energy of the ultrasound may be about 5 W/cm$^2$ or higher.

According to an additional embodiment of the present disclosure, a greater electric field may be generated and a magnitude of an electric stimulus may be increased by embedding a human body-compatible high-k material into a matrix.

An ultrasonic powered neural stimulating device without power sources and lead wires according to the additional embodiment of the present disclosure includes: a time-limited polymer film of a porous structure that is inserted into a body and wound around a nerve; a high-k material embedded in the time-limited polymer film of the porous structure; and an ultrasound generator that generates an ultrasound and applies the ultrasound to the polymer film from the outside of the body.

The time-limited polymer film of the porous structure includes at least one of polylactic acid (PLA), polycaprolactone (PCL), poly(vinyl alcohol) (PVA), polylactide-co-glycolide (PLGA), or poly(3-hydroxybutyrate-co-3-hydroxyvalerate) (PHBV).

The high-k material includes at least one of barium titanate (BTO) or calcium copper titanate (CCTO). As such a high-k material, the high-k material having the human body compatibility is used.

An ultrasound having a wavelength equal to or greater than a thickness of the time-limited polymer film of the porous structure is used as the ultrasound. When the wavelength of the ultrasound is equal to or greater than the thickness of the time-limited polymer film of the porous structure, the ultrasound causes a change in the thickness while passing through the polymer film, and a change in a dielectric constant occurs based on the change in the thickness, so that an electric field may be generated and neural stimulation may be achieved.

The ultrasound generator generates an ultrasound having a frequency in a range from 20 to 50 kHz to perform a neural stimulation treatment. In this case, energy of the ultrasound is about 1 W/cm$^2$.

The ultrasound generator may decompose the time-limited polymer of the porous structure by applying high intensity focused ultrasound (HIFU) having a frequency equal to or higher than 4 MHz to the polymer. In this case, the energy of the ultrasound may be about 5 W/cm$^2$ or higher.

Hereinafter, the present disclosure will be additionally described along with a specific example.

Example 1

Figure 2:
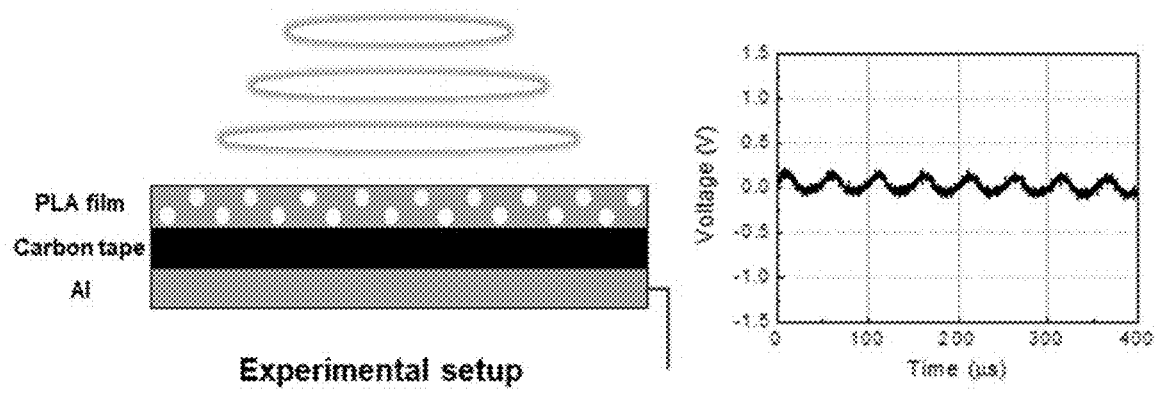
FIG. 2 shows a structure of an ultrasonic powered power generating device manufactured in order to identify contents of the present disclosure and a result of an electrical output thereof.

FIG. 2 shows a structure of an ultrasonic powered power generating device manufactured in order to identify contents of the present disclosure and a result of an electrical output thereof. FIG. 2 shows a structure of an ultrasonic powered power generating device having a size of 2 cm×2 cm and data obtained by measuring a voltage generated when an ultrasound having a frequency of 20 kHz is applied at an intensity of 1 W/cm$^2$. It was identified based on an RMS value that voltage of 76.3 mV was generated.

Figure 3:
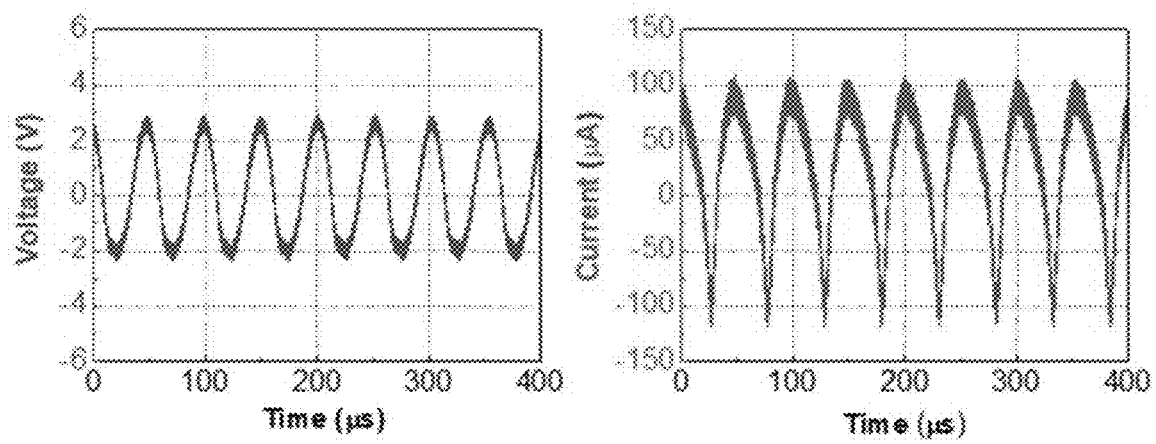
FIG. 3 shows an electrical output value of an ultrasonic powered power generating device in which a human body-compatible high-k material is embedded.

FIG. 3 shows an electrical output value of an ultrasonic powered power generating device in which a human body-compatible high-k material is embedded. FIG. 3 is an electrical output result when the human body-compatible high-k material (BTO) is embedded in the matrix in the ultrasonic powered power generating device having the same structure as in FIG. 2. It is data obtained by measuring the voltage generated when the ultrasound having the frequency of 20 kHz is applied with the intensity of 1 W/cm$^2$. It was identified based on the RMS value that voltage of 2.012V and current of 56.73 μA were generated.

Figure 4:
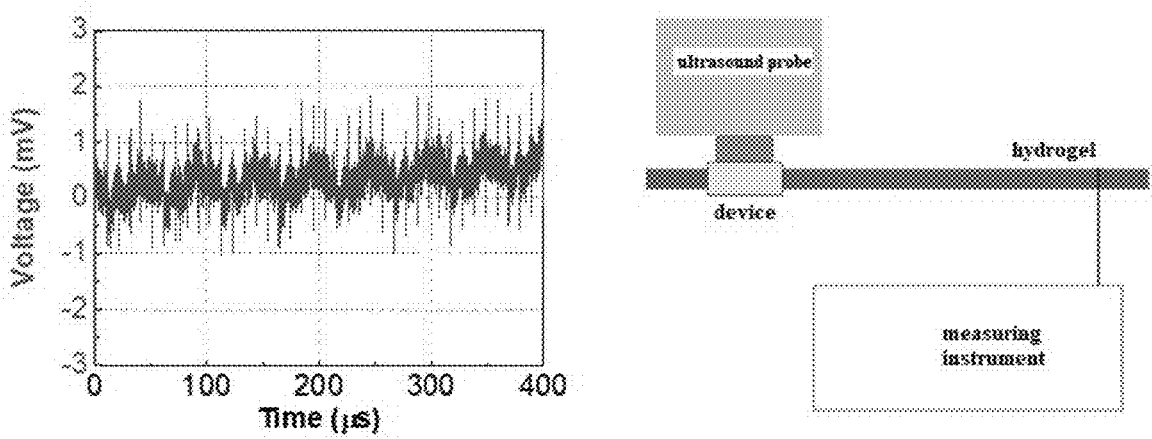
FIG. 4 is a result of an electrical output when a 1 cm×1 cm porous time-limited polymer film is wound around a pAAm hydrogel having a resistance similar to that of a nerve and an ultrasound is applied to the pAAm hydrogel.

FIG. 4 is a result of an electrical output when a 1 cm×1 cm porous time-limited polymer film is wound around a pAAm hydrogel having a resistance similar to that of a nerve and an ultrasound is applied to the pAAm hydrogel. It was identified based on the RMS value that current of 0.89 mV was generated.

Figure 5:
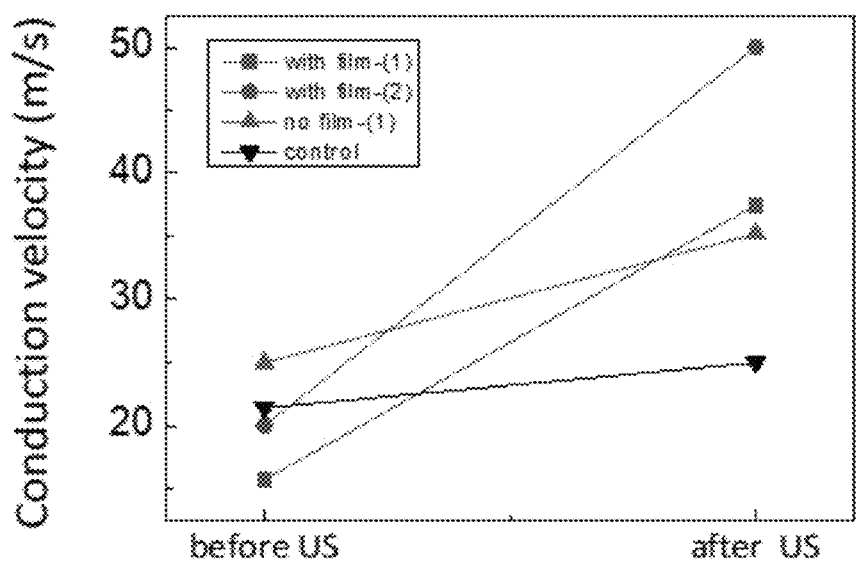
FIG. 5, as a result of verifying nerve treatment effects of rats with a film wound and with no film wound, is data verifying treatment effects depending on a presence or an absence of a device and an ultrasound.

FIG. 5, as a result of verifying nerve treatment effects of rats with a film wound and with no film wound, is data verifying treatment effects depending on a presence or an absence of a device and an ultrasound. With film refers to a case in which the device is wound around the nerve and the ultrasound is applied to the nerve, no film refers to a case in which the ultrasound is applied in an absence of the device, and control refers to a case in which there is no device and no ultrasound is applied to the nerve. The treatment effect was 2.45 times in the case of the with film, the treatment effect was 1.4 times in the case of the no film, and the treatment effect was 1.17 times in the case of control.

According to the present disclosure, the ultrasonic powered device using the time-limited polymer of the porous structure may wind a thin time-limited polymer of a porous structure of a size appropriate for a target nerve around the nerve and stimulate the nerve using the ultrasound from the outside of the body. Unlike conventional neural stimulating devices, because only the thin polymer has to be wound without the lead wire and the cuff electrode, there is no restriction on a surgical position and a process is simple. In addition, because the battery is not used, the device may be miniaturized, which burdens the patient little. Further, because the time-limited material is decomposed in the body, the reoperation is not required to remove the device, which is effective in reducing mental and physical stress of the patient. The present disclosure is expected to present a new paradigm in the neural stimulation and treatment in that the limitations of the conventional neural stimulating devices are overcame, and is expected to be meaningful in terms of commercialization as a power source that is harmless to the human body is used.

In the above, although the description has made with reference to the preferred embodiment of the present disclosure, those skilled in the art will understand that various modifications and changes may be made to the present disclosure without departing from the spirit and scope of the present disclosure as set forth in the following claims.

What is claimed is:

1. An ultrasonic powered neural stimulating device without power sources and lead wires, the neural stimulating device comprising:
    a time-limited polymer film comprising a porous structure and configured to be inserted into a body and wound around a nerve of the body; and
    an ultrasound generator configured to be disposed outside the body and generate ultrasound directed toward the time-limited polymer film wound around the nerve,
    wherein, in response to a wavelength of the ultrasound being equal to or greater than a thickness of the time-limited polymer film, a change in the thickness of the time-limited polymer occurs as the ultrasound passes therethrough,
    wherein, in response to the change in the thickness of the time-limited polymer film, a change in a dielectric constant occurs and an electric field is generated due to the change in the dielectric constant, and
    wherein the electric field stimulates the nerve.

2. The neural stimulating device of claim 1, wherein the time-limited polymer film comprises at least one of polylactic acid (PLA), polycaprolactone (PCL), poly(vinyl alcohol) (PVA), polylactide-co-glycolide (PLGA), or poly(3-hydroxybutyrate-co-3-hydroxyvalerate) (PHBV).

3. The neural stimulating device of claim 1,
    wherein the ultrasound generated by the ultrasound generator includes a frequency configured to perform a neural stimulation treatment, and
    wherein the frequency of the generated ultrasound includes a range from 20 to 50 KHz.

4. The neural stimulating device of claim 1,
    wherein the ultrasound generator is further configured to generate high intensity focused ultrasound (HIFU) having a frequency equal to or higher than 4 MHz to the time-limited polymer film, and
    wherein the HIFU is configured to decompose the time-limited polymer.

* * * * *